(12) United States Patent
Williams et al.

(10) Patent No.: US 9,103,817 B2
(45) Date of Patent: Aug. 11, 2015

(54) METHOD OF DETERMINING THE POINT AT WHICH COAGULATING BLOOD FORMS A CLOT

(75) Inventors: Phylip Rhodri Williams, Swansea (GB); Adrian Evans, Dyfed (GB)

(73) Assignee: Haemometrics Limited (GB)

( * ) Notice: Subject to any disclaimer, the term of this patent is extended or adjusted under 35 U.S.C. 154(b) by 1812 days.

(21) Appl. No.: 11/912,196

(22) PCT Filed: Apr. 20, 2006

(86) PCT No.: PCT/GB2006/001452
§ 371 (c)(1),
(2), (4) Date: Jan. 6, 2009

(87) PCT Pub. No.: WO2006/111758
PCT Pub. Date: Oct. 26, 2006

(65) Prior Publication Data
US 2009/0176261 A1    Jul. 9, 2009

(30) Foreign Application Priority Data
Apr. 20, 2005   (GB) .................................. 0507981.9

(51) Int. Cl.
*C12Q 1/56* (2006.01)
*G01N 33/49* (2006.01)

(52) U.S. Cl.
CPC .......... *G01N 33/491* (2013.01); *G01N 33/4905* (2013.01)

(58) Field of Classification Search
CPC .... G01N 33/491; A61L 24/43; A61L 24/106; A61L 26/28; C08L 77/04; A01N 1/02
See application file for complete search history.

(56) References Cited

U.S. PATENT DOCUMENTS

| | | | |
|---|---|---|---|
| 4,154,093 A | 5/1979 | Smith et al. | 73/54 |
| 4,862,735 A | 9/1989 | Williams et al. | 73/54 |
| 5,253,513 A * | 10/1993 | Van Arsdale et al. | 73/54.41 |
| 5,691,160 A * | 11/1997 | Janmey et al. | 435/13 |
| 2002/0168294 A1 | 11/2002 | Carr et al. | 422/73 |

FOREIGN PATENT DOCUMENTS

| | | |
|---|---|---|
| SU | 1485064 | 6/1989 |
| WO | WO 2006/067504 | 6/2006 |

OTHER PUBLICATIONS

Williams P.R. et al., New techniques in sol-gel characterization—Mechanical measurements and fractal characteristics, Jouranl of Non-Crystalline Solids, 2001, vol. 293-295, pp. 731-745.*
Ikemoto et al. (1982) "Effect of Urokinase on Viscoelasticity of Blood Clot" *Jikeikai Med. J.* 29:1, pp. 83-90.
Raghavan et al. (1996) "Rheological study of crosslinking and gelation in chlorobutyl elastomer systems" *Polymer*, 37:26, pp. 5869-5875. Elsevier Science Ltd. (1996).
Ryan et al. (1999) "Structural Origins of Fibrin Clot Rheology" *Biophys. J.*, 77:5, pp. 2813-2826.
Holly et al. (1988) "Fourier Transform Mechanical Spectroscopy of Viscoelastic Materials With Transient Structure", *J. Non-Newtonian Fluid Mech.*, 27:1, pp. 17-26.
Kudryashov et al. (2001) "Monitoring of Acidified Milk Gel Formation by Ultrasonic Shear Wave Measurements. High-Frequency Viscoelastic Moduli of Milk and Acidified Milk Gel", *J. Dairy Sci.*, 84:2, pp. 375-388.
Iwata et al. (2000) "Antithrombogenicity of cultured endothelial cell-detached surface", Colloids and Surfaces B:Biointerfaces 19, pp. 219-226, Elsevier Science B.V. (2000).
Fukada, E. et al., "Rheological Measurements of Fibrin Gels During Clotting",Thrombosis Research, 1976, pp. 49-58, Suppl. II, vol. 8, Pergamon Press, Inc., United States.
Kaibara, M., "Rheological Studies on Blood Coagulation and Network Formation of Fibrin", Polymer Gels and Networks 2, 1994, pp. 1-28, Elsevier Science Limited, Great Britain.
Winter, H.H., "Gel Point", Encyc. of Polymer Sci. and Tech., pp. 132-145, John Wiley & Sons, Inc., published online Oct. 15, 2003.
Nishinari, K., "Rheological and DSC study of sol-gel transition in aqueous dispersions of industrially important polymers and colloids", Colloid Polym. Sci., 1997, pp. 1093-1107, Steinkopff Verlag.

* cited by examiner

*Primary Examiner* — Satyendra Singh
(74) *Attorney, Agent, or Firm* — Emily A. Shouse; Patterson Intellectual Property Law, PC

(57) ABSTRACT

The present invention is concerned with a method and apparatus for determining the instant at which coagulating blood forms a clot—the primary function of a clot being to act as a hemostatic plug at the site of a lesion in the circulatory system. The method comprises applying a harmonically time-varying stress and strain of controlled amplitude and frequency to the blood using a rheometer and through the use of the Chambon-Winter Gel Equation, the method is capable of determining the gel point which precedes the clotting time indicated by a thromboelastograph.

6 Claims, 6 Drawing Sheets

METHOD OF DETERMINING THE POINT AT WHICH COAGULATING BLOOD FORMS A CLOT

Figure 1:
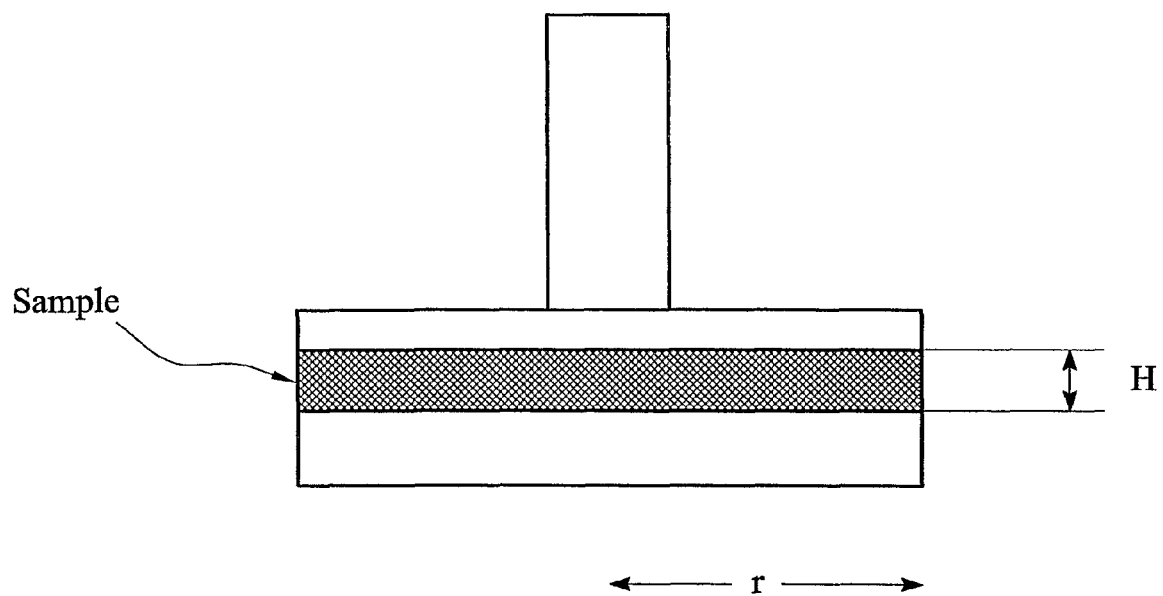
Figure 2:
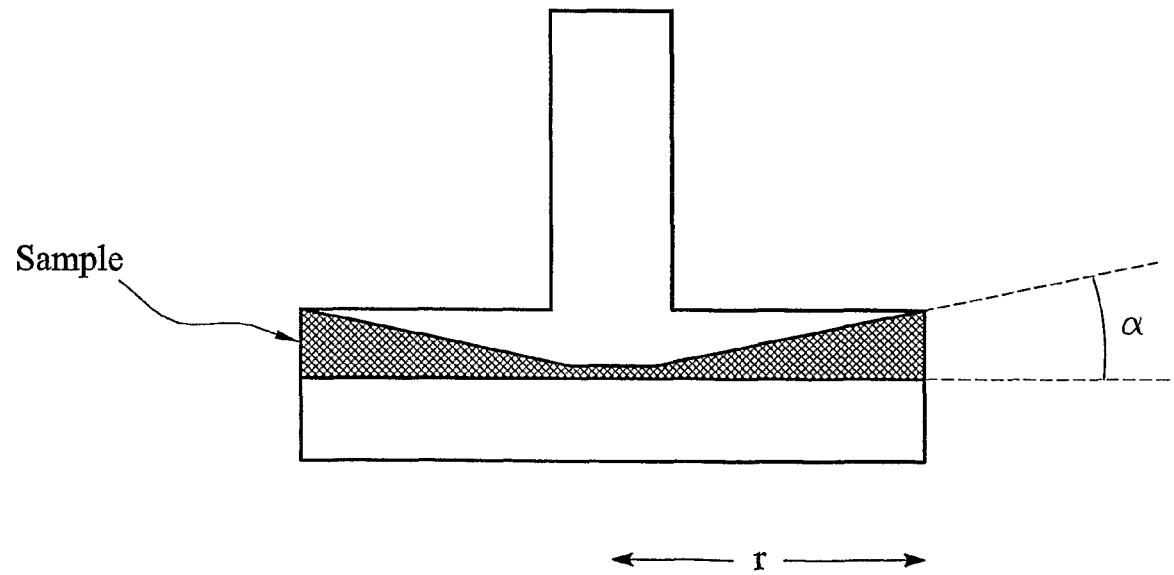

The present invention is concerned with a method and apparatus for determining the point (i.e. the instant) at which coagulating blood forms a clot—the primary function of a clot being to act as a hemostatic plug at the site of a lesion in the circulatory system.

Blood coagulation involves the interaction of blood platelets with calcium ions and conversion of the protein prothrombin into thrombin, a proteolytic enzyme which converts fibrinogen into fibrin. The latter forms a network of 'fibrils' which causes blood to gel. Clot network microstructure is influenced by varying the concentrations of fibrinogen, thrombin and calcium ions; and cross-link formation ('ligation') may be controlled using a highly specific inhibitor of the procoagulant plasma factor FXIIIa. Coagulation may be influenced by thirty (or more) factors, but it is useful to focus on the following factors which are particularly important in regulating clot rheology:

(i) Fibrinogen concentration. Changes in clot deformability have been mooted as a possible explanation for the epidemiological association between plasma fibrinogen concentration and myocardial infarction. The increased incidence of myocardial infarction in patients with elevated levels of fibrinogen has been attributed, in part, to the less deformable clots formed at those concentrations. The elevation of clot rigidities by increased fibrinogen concentrations has been claimed to involve the establishment of greater fibrin fibre and branchpoint densities. The latter claim is based on analysis of SEM images of fibrin clots but the preparation of clots for SEM involves several stages which may have a bearing on the outcome of attempts to interpret their microstructure. These involve successive fixing, dehydrating, critical-point drying and sputter-coating procedures. A further observation made on the basis of SEM is that at high concentrations of fibrinogen, clot structure becomes more 'densely packed' and it has been mooted that this may contribute to limited fibrinolysis. The application of a fractal analysis of live, undessicated clots could prove extremely valuable in establishing the validity of such observations.

(ii) Fibrin network architecture: ligation of fibrin, fibres. Polymerisation and gelation also occur in the absence of thrombin due to the ligation of fibrinogen by activated plasma factor XIIIa. An important conclusion of previous SEM studies is that qualitative differences between the morphology of ligated and unligated clot networks are difficult to detect visually, and that no change is apparent in the general appearance of SEM images of fibrin networks which are stabilised by FXIIIa. This is a provocative finding insofar as FXIIIa is known to enhance clot rigidity. Another important point which emerges from previous work is that the 'stiffness' of clot networks appears to depend strongly on their branching characteristics, and that greater branching occurs at high thrombin or low calcium concentrations. However, in SEM work, the clot structures deemed to be responsible for maximum thrombin-associated rigidities and peak calcium-associated 'stifnesses' are essentially indistinguishable.

At present, the effects of fibrinogen concentration vis a vis those of thrombin concentration on the "organisation" of clot network structure are unresolved and await further study. But it is clearly important to address these issues using an appropriate quantitative morphological analysis of data obtained on undessicated live clot microstructures.

Various pathologies are associated with changes in the viscoelasticity of blood clots and a comprehensive understanding of the relationships between clot microstructure and viscoelasticity has been sought for more than 50 years. This goal remains largely unrealised, due principally to the difficulty of characterising the highly disordered microstructure of clots, and its description in conventional morphological terms. Although the microstructure of fibrin gels (the primary structural component of clots) has been studied by microscopy and light scattering techniques, the latter are restricted to dilute systems, while sample preparation for microscopy may damage gel structure. Rheological measurements, however, can be applied to highly concentrated systems, such as whole blood.

The most widely used instrument in rheological studies of blood coagulation is an oscillating-cylinder device called a thromboelastograph (TEG), which provides a qualitative indication of clot 'rigidity'. TEG measurements transgress the non-linear viscoelastic regime, thereby modifying clot microstructure (and hence rheology) during measurements. More sophisticated oscillatory shear rheometers have been employed to study coagulation but most of the latter studies have employed a single test frequency. Consequently, much potentially valuable information pertaining to clot microstructure is lost, particularly at the Gel Point (GP). The GP describes the transition from the short range connectivity characteristic of a viscoelastic fluid system, to the establishment of a 3-dimensional, sample-spanning network structure characteristic of a wide range of chemical, physical and colloidal gels. The potential significance of the GP in terms of blood clots is its identification with the establishment of a self-similar, fractal gel microstructure.

Qualitative descriptions of clots based on the examination of micrographs refer in loosely defined descriptive terms to the "tightness" or "denseness" or "looseness" or "openess" of their highly disordered microstructures; and in this respect fractal geometry could provide a framework for quantifying the evident structural complexity of clots. Fractal analysis, which describes self-similar structures with a range of length scales for which a non-integer 'fractal dimension' ($d_f$) can be defined, has been applied to aggregate structures in protein gels and some physiological systems. Microscopy of fibrinogen-thrombin gels and light-scattering measurements on thrombin-induced fibrin gelation suggest a self-similar structure appropriate to a fractal analysis but are restricted to dilute systems. Moreover, in the context of blood coagulation, it is the relationships between clot microstructure and mechanical properties which are of prime concern and no ready theory exists to link the latter to the results of light-scattering studies.

The goal of relating the microstructure of blood clots and their viscoelastic properties has been remained largely unrealised, due to the difficulty of describing the complex gel microstructure of blood clots in conventional morphological terms, and a lack of appropriate rheological techniques. The significance of this issue arises from findings that pathologies such as myocardial infraction, peripheral vascular disease, cancer and diabetes are associated with changes in the viscoelasticity of blood clots. However, the present inability to relate these changes to underlying microstructural changes prevents the development of a sufficient understanding of the processes involved. Substantive progress in rheological aspects of blood coagulation research now requires a conjunction of advances in two related areas. The first involves the development of improved rheometry; the second involves the development of a quantitative morphological analysis appropriate to the highly disordered microstructure of blood clots.

In order to address this issue, we have conducted rheological studies of blood coagulation which yield structural information, based on a fractal analysis of the viscoelastic properties of blood clots formed at the gel point, GP.

Therefore, according to the present invention, there is provided a method of determining the point at which a clot forms in coagulating blood, which method includes:
a) Providing a sample of blood;
b) Simultaneously carrying out the following steps:
   i) applying a harmonically time-varying stress (of controlled amplitude and frequency) to the blood at a predetermined first frequency and measuring the corresponding phase and amplitude of the resulting first strain output;
   ii) applying a harmonically time-varying stress (of controlled amplitude and frequency) to the blood at a predetermined second frequency and measuring the corresponding phase and amplitude of the resulting second strain output;
   iii) applying a harmonically time-varying strain (of controlled amplitude and frequency) to the blood at a predetermined first frequency and measuring the corresponding phase and amplitude of the resulting first stress output;
   iv) applying a harmonically time-varying strain (of controlled amplitude and frequency) to the blood at a predetermined second frequency and measuring the corresponding phase and amplitude of the resulting second stress output;
c) Utilising the power-law form given by the Chambon-Winter Gel Equation (1986):

$$G(t) = St^{-\alpha}$$

where S is a 'gel-strength' parameter and $\alpha$, the viscoelastic stress relaxation exponent, has values in the range $0 < \alpha < 1$. The corresponding relationship in small amplitude oscillatory shear is $$G'(\omega) = G''(\omega)/(\tan \alpha\pi/2)$$

where G' is the dynamic rigidity (or shear storage modulus) and G" is the loss modulus. The dynamic moduli G' and G" are proportional to $\omega^\alpha$ and thus, at the gel point, the loss tangent (tan $\delta$=G"/G') calculated for each frequency applied in b) and c) is therefore independent of frequency at the Gel Point; G' and G" are the components of the complex shear modulus G*($\omega$) (G*=G'+iG") where $\omega$ is the angular frequency of the oscillation; and
d) Monitoring the change in tan delta (tan $\delta$) with time to establish the time at which tan delta is the same irrespective of the frequency applied in b) and c) so as to establish the time when the blood first forms a clot.

The gel point is that instant at which a sample of coagulating blood undergoing gelation changes from one in which only short-range connectivity is present, to one in which a 3-dimensional structure is sample-spanning. The significance of the gel point in terms of coagulation is that it allows the instant of clot formation to be defined unequivocally within the theory of linear viscoelasticity, in terms of the Gel Equation wherein the stress relaxation exponent a has values in the range $0 < \alpha < 1$. Advantageously, the results for clots formed utilising the method of the present invention is that the values of $\alpha$ are in this range.

A particular advantage of the present invention is that it provides a method that is capable of determining the gel point of coagulating blood which precedes the clotting time indicated by a TEG.

The identification of the gel point with the establishment of a self-similar, fractal microstructure has particular significance in the context of blood coagulation. Many previous workers in the field of measurement of blood coagulation has resorted to qualitative descriptions such as 'denseness' or 'tightness' or 'loosening up' of clot structure. Clots have also been referred to as having 'coarse' or 'fine' microstructures. In this respect fractal geometry provides a vital role. Accordingly, by identifying the point at which coagulating blood forms a clot utilising the method according to the present invention, there is provided a framework for the quantification of structural complexity in clots formed under a range of biophysical and biochemical conditions.

It is particularly preferred that the method according to the present invention is carried out using a rheometer of the controlled, forced non-resonant oscillatory displacement ("controlled strain") or oscillatory torque ("controlled stress") type.

Preferably, the rheometer of controlled strain type is one such as a Rheometrics ARES (Advanced Rheometric Expansion System), a rheometer designed to perform both steady and dynamic measurements. An important feature of this rheometer is that it has both STRAIN IN and TORQUE OUT electrical signal sockets, features which allows the user to perform their own calculations upon 'raw' (unprocessed) data without relying on the rheometers analysis software.

The Rheometrics ARES (Advanced Rheometric Expansion System) Controlled Strain Rheometer (Rheometric Scientific Inc.) is a mechanical spectrometer capable of operating in either a dynamic (oscillatory) mode or steady shear mode. The instrument principally comprises of an actuator, a torque and normal force transducer and an environmental system.

Typical rheometers which may be used in the method according to the present invention, may include a low shear actuator, a force rebalance transducer and an environmental system.

The low-shear actuator is especially suited for low shear measurements which are necessary for strain-sensitive materials. This direct-drive, DC Servo actuator may operate in dynamic mode and has an angular displacement range of 0.000005 to 0.5 radians and a frequency range of $1.59 \times 10^{-6}$ Hz to 15.9 Hz with a resolution of 0.098% of commanded frequency.

The Force Rebalance Transducer, with 'normal force 2K FRTN1', consists of independent torque and normal force servo control systems, each utilising position feedback to maintain the transducer shaft in a null position when no force is applied. When a force is applied to the transducer shaft, the servo control systems drive the shaft back to a null position. The current required to drive back to null position is proportional to the amount of force applied. This current is converted to a DC voltage which is scaled to become the torque output of the rheometer [Ares Instrument Manual, Rheometric Scientific Inc, 2000].

The 2K FRTN1 transducer is capable of operating in two torque ranges; a high torque range of 2 to 2000 g·cm and a low torque range of 0.02 to 200 g·cm. In low torque range the transducer functions in increments of 0.00008 g·cm. The normal force measurement system has a range of 2 to 2000 gmf. The maximum operating frequency of the transducer is 15.9 Hz.

The transducers are air-lubricated and therefore have essentially no compliance. For this reason high quality air (particles <5 microns in diameter, relative humidity=35 to 75%, dewpoint=10° C.) is supplied to the rheometer at a pressure of 80 psi (5.5 bar).

An environmental system is necessary for precise control of the sample temperature. The ARES Rheometer has two environmental systems available; a forced air convection oven and a re-circulating fluid bath.

The oven is a forced air convection chamber that encloses the sample and has a dual-element heater with counter-rotating air flow for a wide temperature range (−150° C. to 600° C.) and precise temperature control (±0.35° C.). Liquid Nitrogen may be used to achieve the sub zero temperatures.

The desired sample temperature is maintained by a control loop that is closed around a platinum resistive thermometer (PRT). This PRT is installed on the lower fixture of the geometry (Parallel Plate and Cone and Plate types) and the electrical resistance of the PRT changes with temperature. Another PRT is installed inside the oven chamber which allows the operator to choose whether to control the actual oven temperature or the temperature of the lower fixture.

A re-circulating fluid bath may be more appropriate for temperature control for samples which may experience evaporation caused by circulating air. The fluid bath controls the sample temperature using a closed fluid re-circulating system. The fluid used is distilled water and allows a controlled temperature range of 1° C. to 99° C. The lower test fixture of the geometry is mounted within the fully-enclosed bath through which flows the water supplied by a circulator. Either the actual water temperature may be controlled or for more precise control of the sample temperature a PRT is installed on the lower fixture. The fluid bath is compatible with Parallel Plate, Cone and Plate, and couette type geometries and allows a temperature control of ±0.35° C.

Preferably, the rheometer of controlled stress type is one such as a TA Instruments CSL. The rheometer and ancillary equipment required for its operation consist of the seven main components detailed below:

(1) An air bearing, which supports and centres the rotating spindle, incorporating an electronically controlled induction motor. The air bearing prevents any contact between fixed and moving parts.
(2) A hollow spindle incorporating a threaded draw rod, onto which the required measuring geometry is secured.
(3) A digital encoder sensing angular displacement ($10^{-4}$ radians nominal). The encoder consists of a light source and a photocell arranged either side or a transparent disc attached to the spindle. Fine lines similar to diffraction grating lines, are photographically etched around the disc edge. Through the use of a stationary diffraction grating between the light source and the disc, diffraction patterns are set up as the disc moves under applied torque which are directly related to the angular displacement. The optical encoder determines the displacement of the measuring geometry, from which values of displacement are obtained.
(4) A non-rotating lower platen of the measuring assembly, on a height adjustable pneumatic ram with micrometer fine adjustment, which may be raised to provide the desired gap height setting.
(5) A temperature control unit incorporated within the lower plate. The system is a peltier type, using a thermoelectric effect functioning as a heat pump with no moving parts. This enables temperatures up to 15° C. lower than the temperature of the cooling water to be precisely held. Control of the magnitude and direction of the electrical current allows the desired temperature adjustment within the lower platen (control to 0.1° C.), and thus the sample, when both cone and plate and parallel plate geometries are employed.

Rheometers which may be used to carry out the method according to the present invention may have any one of a number of known geometries.

The selection of type of measuring geometry is a very important consideration and depends on certain sample properties (including shear viscosity, presence of particles, evaporation effects) and these determine the shear rate and torque (or stress) ranges of the instrument. Each geometry has its own Strain Factor and Stress Factor which are used by the rheometer software to calculate the actual Stress and Strain from the experimentally achieved values of torque and displacement respectively. These factors depend on the dimensions of the geometry and also the type of geometry employed. Each types are described in this section together with their governing equations. The stresses and strains are then calculated using the appropriate geometry form factor using the following two equations:

$$\sigma = K_\sigma \cdot T \tag{3.1}$$

where
 σ is the shear stress (Pa)
 $K_\sigma$ is the stress form factor for the geometry of interest
 T is the torque (Nm)
and $$\gamma = K_\gamma \cdot \theta \tag{3.2}$$

where
 γ is the shear strain
 $K_\gamma$ is the strain form factor for the geometry of interest
 θ is the angular displacement (rad)

There are three main types of geometry. These are parallel plate, cone and plate and the Mooney-Ewart system. Other geometries employed on rotational viscometers include the standard couette or 'bob and cup' and various forms of single and double concentric cylinder systems. These geometries are preferably made of stainless steel or titanium or aluminium or polycarbonate or acrylic or perspex and may be gold-coated and have roughened surfaces to overcome wall-depletion ('slip') effects.

A parallel plate system consists of two flat plates situated parallel to each other. Parallel plate geometries may be used when the material contains large particles or aggregates. A gap to maximum particle size ratio of >100 is desirable to ensure the adequate measurement of bulk material properties [Van Wazer 1963]. Parallel plate geometries also allow different gap sizes which provides a convenient test for wall slip effects (see FIG. 1).

The shear strain is non-uniform throughout the gap and the greatest strain occurs at the outer edge of the plates, therefore the material at the edge has the greatest influence on the measurement. This can produce significant errors if any evaporation of the test sample occurs.

The shear stress σ and shear strain γ are calculated from the corresponding measured values of torque and displacement using the following form factors:

$$K_\sigma = \frac{2}{\pi r^3} \tag{3.3}$$

where
 r is the plate radius (m)
and $$K_\gamma = \frac{r}{H} \tag{3.4}$$

where
 r is the pate radius (m)
 H is the (shearing) gap between the plates (m)

The cone and plate geometry comprises of an upper cone and a lower flat plate. The upper cone is truncated to reduce the effects of particles causing interference and so there is no contact between the two plates. This truncated section provides a negligible contribution to the total torque. The gap size is very small so this geometry is not desirable for materials consisting of large particles or aggregates. Typical values are cone and plate of diameter of 40 mm and cone radius 2 degrees with a truncated section equal to a gap size of 51 microns.

An important feature of the cone and plate geometry is the homogenous shear rate or linear velocity profile throughout the gap. This simplifies the equations for calculating stresses and strains and can be of great advantage when investigating non-linear viscoelasticity and time-dependent systems [Giacomin and Dealy, 1993].

A disadvantage of the cone and plate geometry is the effect of thermal expansion at large temperature deviations. Since the gap is very small (typically ≈50 microns) any thermal expansion may significantly effect the rheological measurement.

The form factors for the cone and plate geometry are as follows:

$$K_\sigma = \frac{3}{2\pi r^3} \quad (3.5)$$

where:
r is the radius of plate (m)

$$K_\gamma = \frac{1}{\tan\alpha} \quad (3.6)$$

where:
α is the cone angle (rad)
Note That The Symbol α is Used Elsewhere For The Stress Relaxation Exponent in The Gel Equation The standard couette (or bob and cup) geometry is a recessed concentric cylinder system whereby the test sample is maintained in the annulus between two cylinder surfaces. The recessed end or hollow cavity is specifically designed to trap air. The standard couette is best used for low viscosity samples and for those with large particles such as fluid suspensions.

The form factors for the standard couette geometry are as follows (assuming a vary narrow annulus; annular gaps of the order of 10% of the cylinder radius $R_C$, although ambiguity arises over the effective mean radius $R_a$ [Whorlow 1992]):

$$K_\sigma = \frac{1}{2\pi R_a^2 L} \quad (3.7)$$

where:
$R_a$ is the average of the radius of the outer and inner cylinders (m), $R_a = (R_B + R_C)/2$
L is the height of the inner cylinder or bob (m)

$$K_\gamma = \frac{R_a \theta}{R_C - R_B} \quad (3.8)$$

where:
$R_B$ is the radius of the inner cylinder or bob (m)
$R_C$ is the radius of the outer cylinder or cup (m)

The Mooney-Ewart geometry consists of a concentric cylinder system with the inner cylinder having a cone end. The cone end is used to account for end effects and is designed using the following relationship which ensures that the shear rate is homogenous throughout the geometry:

$$\alpha = \tan^{-1}\left(\frac{R_C - R_{ME}}{R_C}\right) \quad (3.9)$$

where
α is the Mooney-Ewart cone angle (rad)
$R_{ME}$ is the radius of the inner cylinder (m)
$R_C$ is the radius of the outer cylinder or cup (m)

The dimensions of the Mooney-Ewart geometry employed by the Carrimed $CSL^2$ 100 Controlled Stress Rheometer are $R_{ME}$=24 mm, $R_C$=25 mm, an immersion height L of 30 mm, and a cone truncation of 35 microns. Due to the shape of the geometry a peltier plate cannot be employed, therefore the geometry is surrounded by a jacket which is attached to an external water bath for adequate temperature control.

The form factors are a result of a combination of the factors for a cone and plate geometry and a standard couette geometry. Mooney (1931) assumed that, for small gaps, the stress, σ, differed relatively little from the arithmetic mean stress [Whorlow 1992].

Shear stress calculations combine $K_\sigma$ for the cone and plate (equation 3.5) and $K_\sigma$ for the cylindrical section (Equation 3.7) in the formula (Carrimed, 1992)

$$K_\sigma(MooneyEwart) = \frac{K_\sigma(\text{cone}) \cdot K_\sigma(\text{cylinder})}{K_\sigma(\text{cone}) - K_\sigma(\text{cylinder})} \quad (3.10)$$

and for the shear strain, $$K_\gamma = \frac{1}{\tan\alpha} \quad (3.11)$$

where
α is the Mooney-Ewart cone angle (rad)

The Geometries available to the Rheometrics ARES are a 25 mm diameter Plate-Plate, 50 mm diameter Plate-Plate, 25 mm diameter 0.1 rad angle Cone-Plate, 25 mm diameter 0.04 rad angle Cone-Plate, 50 mm diameter 0.04 rad angle Cone-Plate, 32 mm diameter bob and 34 mm diameter cup, and a 16.5 mm diameter bob and 17 mm diameter cup. The bob and cup type geometries (or couette type) have a length of 34 mm and 13 mm respectively.

The rheometer, such as the Rheometrics ARES Controlled Strain Rheometer, which is preferably used in the method according to the present invention is capable of operating in a 'Multi-Wave' or a frequency-multiplexed mode known as Fourier Transform Mechanical Spectroscopy, FTMS. This is accomplished by imposing a strain (or stress) waveform composed of more than one harmonic frequency (as designated by the user), and analysing the corresponding stress (or strain, respectively) response by means of a Fourier analysis, to analyse each individual frequency component separately.

FTMS is a frequency 'multiplexing' technique which combines several harmonics of different frequencies and amplitudes to produce a composite non-sinusoidal waveform. In a controlled stress rheometer, torque waveforms incorporating various oscillation frequencies are presented to the test material simultaneously, but the dynamic consequences of each are analysed separately using an appropriate Fourier analysis. In principle, therefore, multi-frequency data may be obtained in a single test using FTMS.

In its most widely implemented form, FTMS was developed by Holly et al. (1988) using a Controlled Strain Rheometer. They showed that multiple frequency values of the dynamic moduli could be obtained successfully in a single test for non-reacting polymeric liquids and a cross linking polydimethylsiloxane (PDMS) gelling system. They concluded that FTMS had advantages over conventional frequency sweep methods (which necessitate measuring the dynamic properties at each frequency consecutively) when dealing with transient systems, due to the decrease in time of the rheological experiment $t_{exp}$.

For a frequency sweep $$t_{exp} = \sum_{f=f_f}^{f=f_h} \frac{\xi_f}{f} \quad (3.19)$$

Where
$\xi$ is the number of cycles per measurement at a frequency f
$f_f$ is the lowest or fundamental frequency in the test (Hz)
$f_h$ is the highest frequency in the test (Hz)
f is the frequency including all frequencies ranging from $f_f$ to $f_h$ (Hz)

For an FTMS test $$t_{exp} = \frac{\xi_{f_f}}{f_f} \quad (3.20)$$

Equations 3.19 and 3.20 illustrate the time saving qualities of the FTMS test.

Clearly, FTMS is a potentially useful tool in attempts to detect the instant of gelation (the Gel Point). In terms of the Winter-Chambon Gel Equation, the Gel Point can be detected by a frequency independent phase angle. Therefore, the multiple frequency capabilities of FTMS make it, in principle, an ideal technique for Gel Point detection.

FTMS has also been applied to other gelling systems [In and Prud'homme 1993, Malkin et al. 1993] and the technique was successfully implemented in a Controlled Stress Rheometer to achieve dynamic properties at multiple frequencies in a single test for a model viscoelastic fluid [Davies and Jones 1994].

The basic aspects of FTMS were first implemented on a Controlled Strain Rheometer by Holly et al. (1988), but the technique may be readily adapted, in principle, to a Controlled Stress Rheometer by simply replacing strain, $\gamma$, with stress, $\sigma$, and vice versa. In FTMS as implemented on a Controlled Stress Rheometer, the material is subjected to an oscillatory stress $\sigma$, $$\sigma = \sum_{i=1}^{m} \sigma(\omega_i) = \sum_{i=1}^{m} \sigma_i \sin\omega_i t \quad (3.24)$$

Where
m is the number of frequency components
$\sigma_i$ is the stress amplitude if the i th component (Pa)
$\omega_i$ is the i th angular frequency component (integer multiples of the fundamental frequency ($\omega_f$) (rad s$^{-1}$)

The resulting (complex) strain response is recorded and broken down into its individual frequency components using an appropriate Fourier analysis (by the Fast Fourier Transform, FFT). From this, the viscoelastic parameters G'($\omega_i$), G"($\omega_i$), and hence phase angle $\delta(\omega_i)$ can be calculated from the individual values of stress and strain at each individual frequency $\omega_i$. A more detailed account of FTMS testing with inertial considerations is given by Davies and Jones (1994).

FTMS tests invoke the Boltzmann Superposition Theory which underlies the Theory of Linear Viscoelasticity. It states that the total strain experienced by a material is equal to the sum of all the changes induced in the material by the applied stress throughout its past history [Ferry, 1980]. It follows that the total stress or strain which is experienced by a material in FTMS testing is equal to the sum of the individual stresses or strains associated with each constituent applied harmonic frequency of the composite FTMS waveform.

Figure 3:
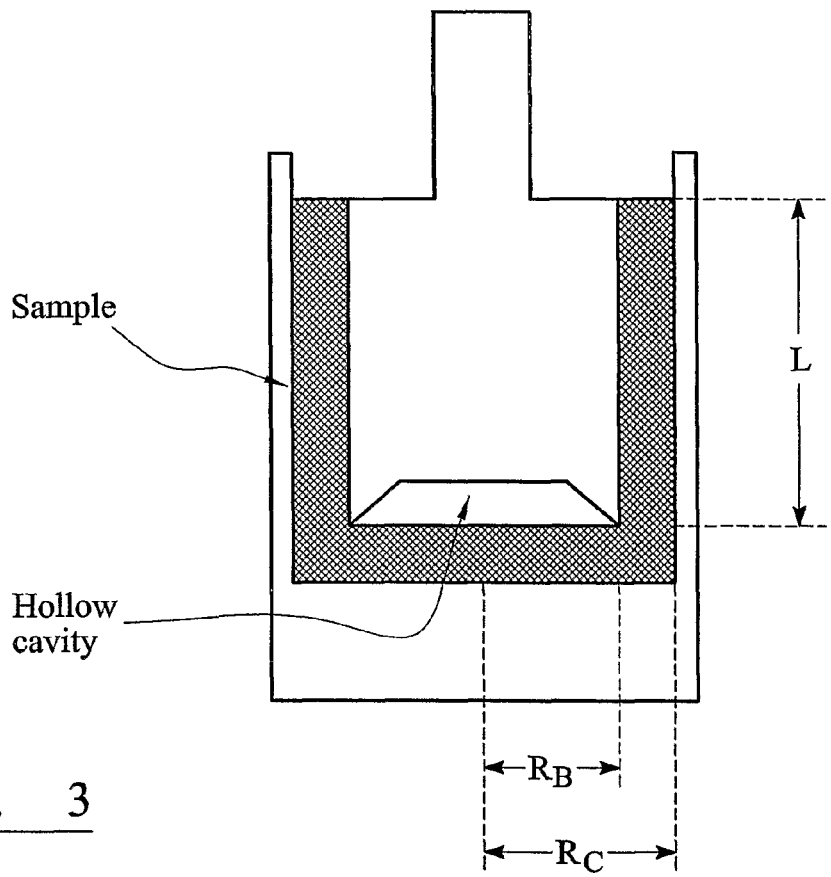
Figure 4:
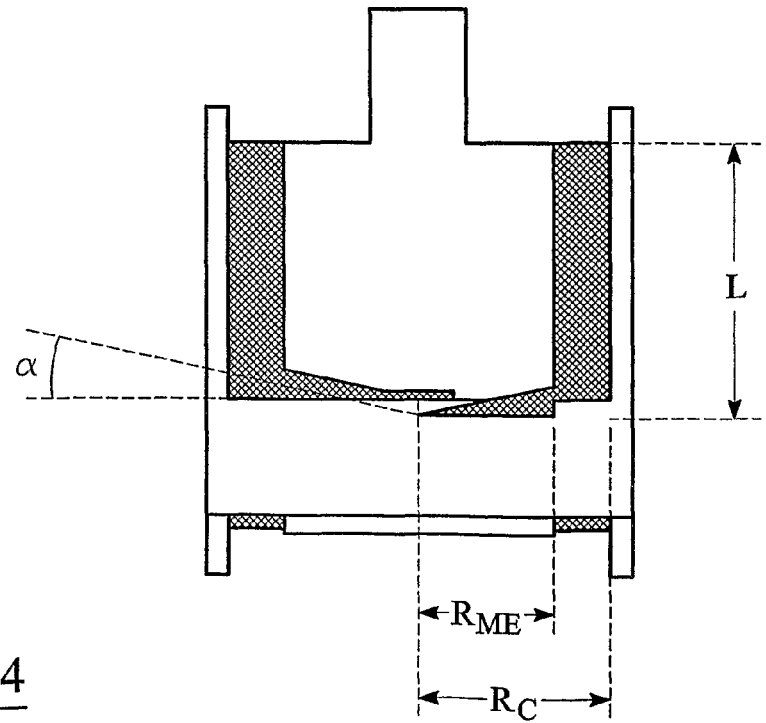
Figure 5:
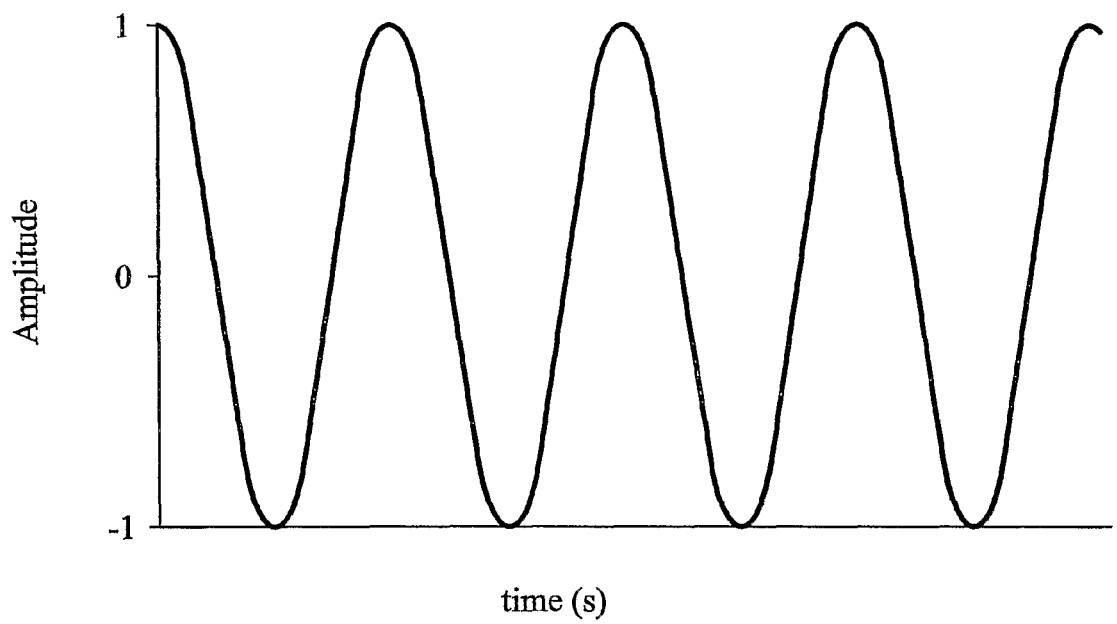
Figure 6:
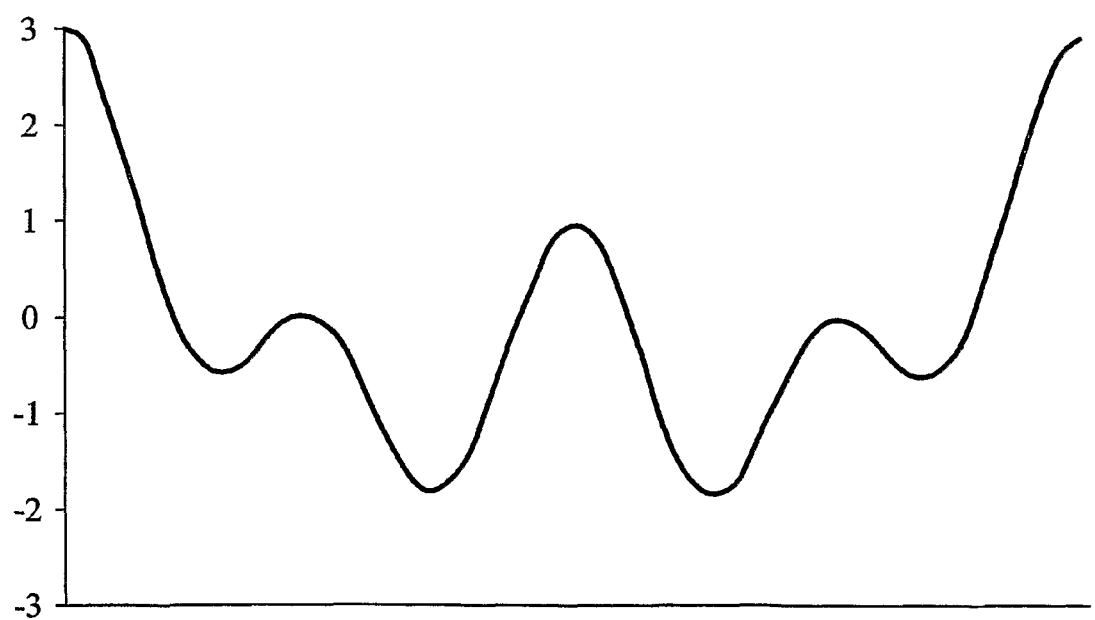

FIGS. 3.6 and 3.7 show the result of combining three harmonic stress waveforms of frequency 1 Hz, 2 Hz, and 4 Hz, each of equal amplitude in this instance, to give a composite stress waveform of amplitude, whose peak amplitude is almost three times greater than that of each of the individual component waveforms.

Since FTMS in only valid within the Linear Viscoelastic Regime, the total stress $\sigma$ (or total strain $\gamma$) must not exceed the critical stress $\sigma_c$ or critical strain $\gamma_c$, respectively. This will limit the number of harmonics that can be used in a single FTMS test because each individual value of strain $\gamma_i$ must be at a resolvable level of displacement for accurate Fourier analysis. Preferably, the strain or stress output corresponding to a stress or strain input, respectively, is measured using Fourier Transform Mechanical Spectroscopy.

Accordingly, there is further provided a use of a rheometer in the measurement of the gel point of coagulating blood.

It is particularly preferred that the measuring geometry of the rheometer has at least one surface in contact with the blood which is a biomimetic surface. The biomimetic surface is typically populated by live endothelial cells and fibroblasts, at the surfaces of the rheometer measuring geometries. This is advantageous in view of the role of fibroblasts in initiating the blood coagulation cascade and the need to study differences in enzymatic reactions at different surfaces. Advantageously, the present invention permits the combination of haematological and rheometrical functionality.

Typically, biomimetic structures such as collagen gels or microporous and nanoporous polymeric substrates (scaffolds), which combine haematological and rheometrical functionality, at the surface of our rheometer measuring geometries are preferred according to the present invention. The biomimetic structures, which consist of microporous polymeric films with regular morphologies, will typically incorporate living cells, including fibroblasts. All blood vessels have a smooth lining of flattened, endothelial cells which are joined in and edge-to-edge configuration. In addition, fibroblasts (the principal cell of the dermis) congregate at wound surfaces and play a vital role in initiating the blood coagulation cascade and promoting efficient healing at the site of a lesion. It is essential to modify rheometer measuring surfaces (i.e. those in contact with blood plasma) to provide physiological relevance and to increase fundamental understanding of the role of different cell types in the blood coagulation process.

The process by which the surfaces could be modified involves the formation of structures (as film coatings on surfaces) due to the interaction of a vapour stream with an appropriate mobile (i.e. low shear viscosity) polymer solution. The process lends itself to structure formation on wetted geometries placed within the vapour stream and cellular species may be incorporated within the film by deposition within solution droplets, or cultured at its surface. Such films can be formed at the surfaces of rheometer measuring geometries, and are readily removed using appropriate solvents following measurements (the geometry may subsequently be re-coated).

The present invention will be exemplified according to the present invention, with reference to the present invention, wherein:

FIG. 1 represents a parallel plate measuring geometry of a rheometer;

FIG. 2 represents a cone and plate measuring geometry of a rheometer;

FIG. 3 represents a standard couette (concentric bob and cup) measuring geometry of a rheometer;

FIG. 4 represents a Mooney-Ewart measuring geometry of a rheometer;

FIG. 5 represents a graph showing the individual harmonic stress (or strain) waveforms to be combined to form a composite waveform which is subsequently applied to the sample of test material (blood);

FIG. 6 represents a graph of a composite wave form produced by combining sinusoids of equal amplitude and frequencies 1 Hz, 2 Hz and 4 Hz.

FIG. 7 represents the criterion of gel point detection based on the occurrence of a G'-G" crossover.

FIG. 8 shows how the use of FTMS allows the gel point to be detected precisely.

FIG. 9 demonstrates the inherent limitations of Thromboelastography (TEG) in the assessment of clot time.

FIG. 10 shows the detection of gel point based on measurements of the loss tangent (G"/G') at several frequencies.

FIG. 11 represents a schematic of a rheometer which can be used according to the present invention.

The present invention will now be further exemplified by the following example,

FIG. 7 represents the criterion of gel point detection based on the occurrence of a G'-G" crossover (the time at which tan δ=1, δ=45 degrees) which is inherently unreliable as the inferred gel time varies with frequency or cannot be detected (see FIG. 7). TEG measurements based on a single (nominal frequency) of oscillation invoke an 'operational' definition of clotting (i.e. gel time) in terms of the attainment of an arbitrary level of instrument output, as recorded on a chart recorder or similar data-logging device. In such a method, the recording of elasticity in units of length (mm) has no intrinsic scientific meaning.

As can be seen from FIG. 8, FTMS allows the gel point to be detected precisely. The frequency independence of tan δ at the gel point is readily established and, according to the invention, can be seen from the present invention. The stress relaxation exponent a can be related to the fractal dimension $d_f$ of the underlying clot microstructure.

FIG. 9 shows aqueous gelatin solutions have well-defined gel point and can be used to demonstrate inherent limitations of Thromboelastography. Although TEG output is (qualitatively) similar to the temporal development of the dynamic rigidity G'(ω), the assessment of 'clot time' by TEG measurements is based on the attainment of an arbitrary (2 mm) level of "clot firmness". Similarly, assessment of 'clot time' based on G' also invokes attainment of arbitrary level of dynamic rigidity at a single specific frequency.

FIG. 10 shows the detection of gel point based on measurements of the loss tangent (G"/G') at several frequencies. The gel point is found to occur prior to the 'clot time' indicated by the TEG. In blood coagulation work this new FTMS approach provides significant 'warning' of incipient clot formation, which can be up to several minutes prior to clot detection by the TEG.

FIG. 11 represents a schematic of a rheometer which can be used according to the present invention.

In order to confirm the effectiveness of the rheometrical data acquisition and digital signal processing protocols used in the methods according to the present invention, a preliminary study was made of the thermo reversible gelation of aqueous gelatine solutions, a system whose behaviour at the GP conforms to the gel equation in terms of the frequency independence of the loss tangent at the Gel Point. Studies were also made of the gelation of fibrin gels formed from solutions of fibrinogen (at physiological concentrations) the gelation (or coagulation) process being activated by the addition of thrombin. The absence of wall depletion ('slip') phenomena was confirmed using different configurations of sample geometry and by comparing the corresponding values of derived dynamic moduli G' and G" (and phase angle, δ) for frequencies in the range 0.1 Hz to 10 Hz. The measurements showed the adequacy of a maximum strain of 10%, using different measuring geometries and configurations (50 mm diameter plate-plate at various gap sizes, and a 50 mm diameter cone-plate system with a 0.04 radian angle) at a temperature of 28° C. The consistency of the data confirmed the absence of wall slip at all test frequencies.

The GP was determined by monitoring the development of the phase angle, δ, at different frequencies throughout the gelation process. Prior to the GP, the system is characterised by visco-elastic fluid-like behaviour, the value of tan δ decreasing with frequency. The post-GP regime is characterised by viscoelastic solid-like behaviour, the value of tan δ increasing with increasing frequency. At the GP, tan δ is frequency independent, its value, in this particular example, being 1.74 (δ=60.1°). The corresponding value of α is 0.67, calculated from the relationship $\delta=\alpha\pi/2$.

Experiments involving blood were conducted using the cone plate geometry at frequencies of 2 Hz, 1 Hz and 0.5 Hz. Prior to each experiment, citrated samples of whole human blood were activated by the addition of 0.2 ml calcium chloride. The frequency independence of tan δ which marks the GP after approx 950 seconds was found to occur at a value of δ of 86°. The corresponding value of α was found to be 0.955. Prior to the GP, the system was viscoelastic liquid-like, whereas the post GP behaviour was clearly viscoelastic solid-like.

In addition to providing structural information pertaining to the clot formed at the GP of coagulating blood, the results of the present example have wider significance in terms of rheological blood coagulation studies.

Firstly, the value of the frequency independent loss tangent recoded at the GP of blood is relatively high (corresponding to δ=86° and α=0.955). Whereas a rheological scaling theory of fractal correlations predicts values of α in the range $0.67<\alpha<1$, experimental values have previously been reported to lie in the range $0.19\leq\alpha\leq0.92$. This high phase angle at the GP of blood serves to highlight the inadequacy and potential dangers of reliance on a gelation time (or clotting time) criterion based on measurements of tan δ at a single frequency oscillation. One such criterion invokes a G'-G" 'crossover' behaviour (where δ=45°, tan δ=1) is widely used and has been adopted in work on the gelation of fibrin-thrombin solutions. The results of the present investigation show this criterion to be inappropriate in the case of blood coagulation: even 400 seconds after the GP, the value of tan δ continues to exceed unity (at each test frequency).

Figure 7:
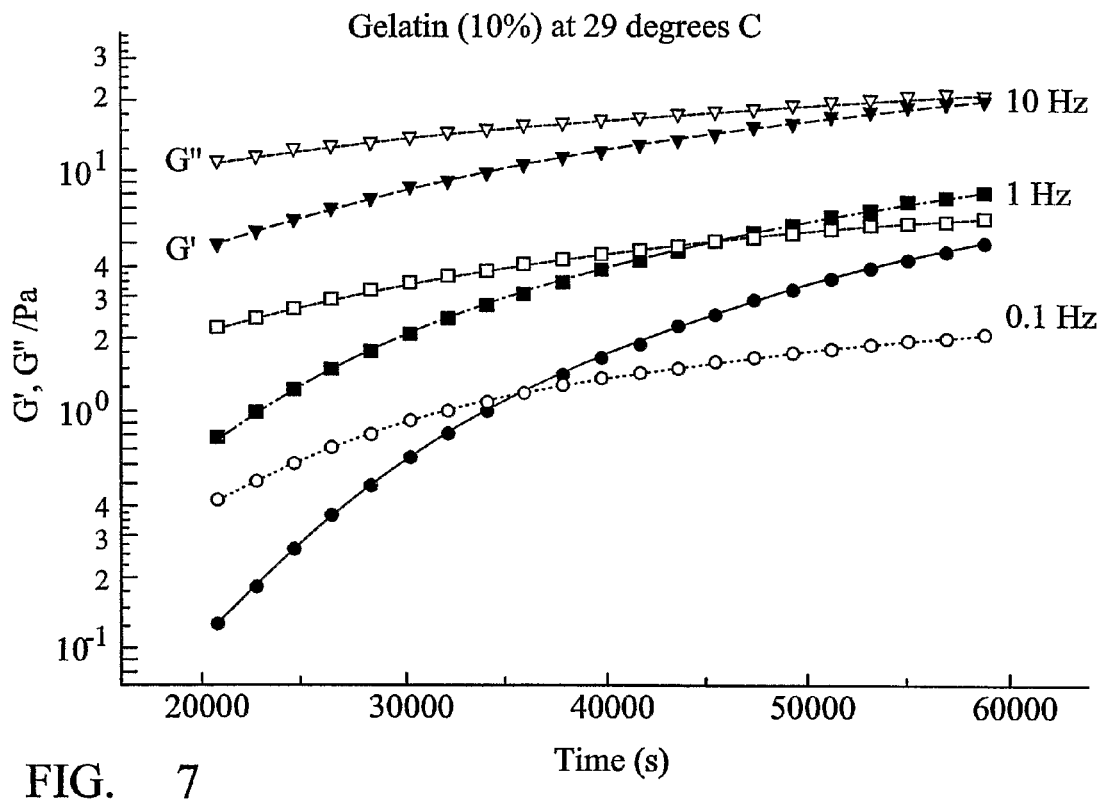
Figure 8:
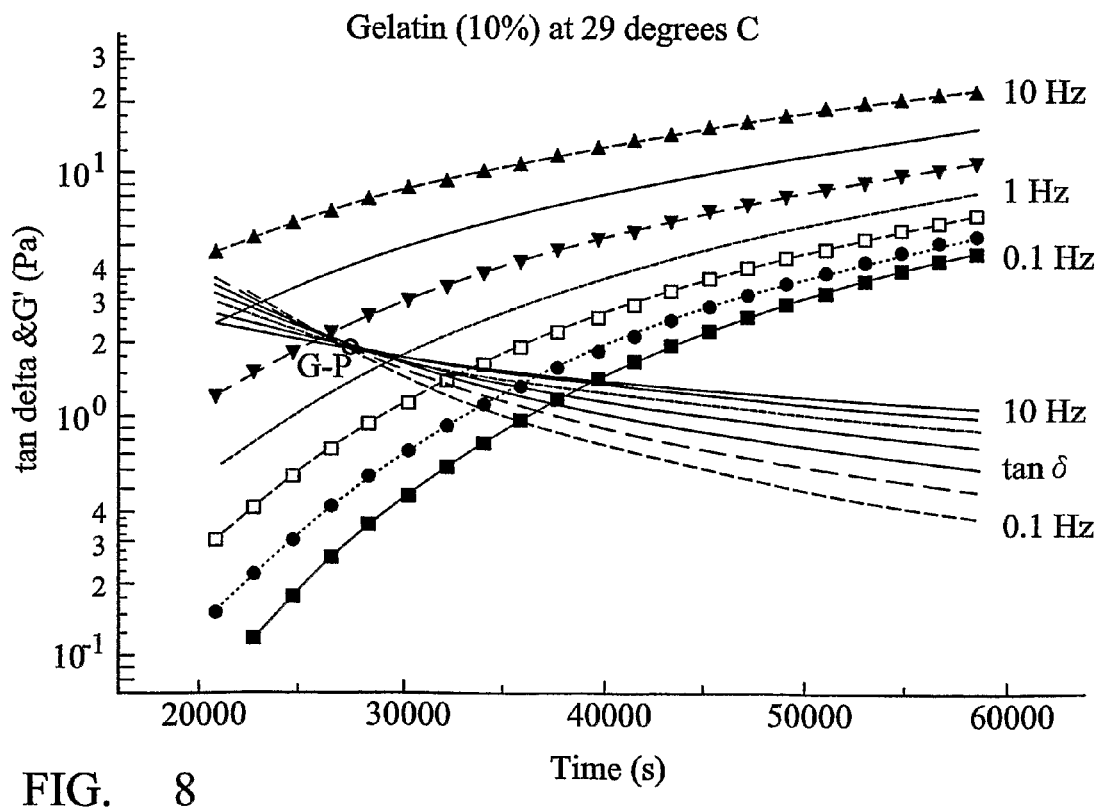
Figure 9:
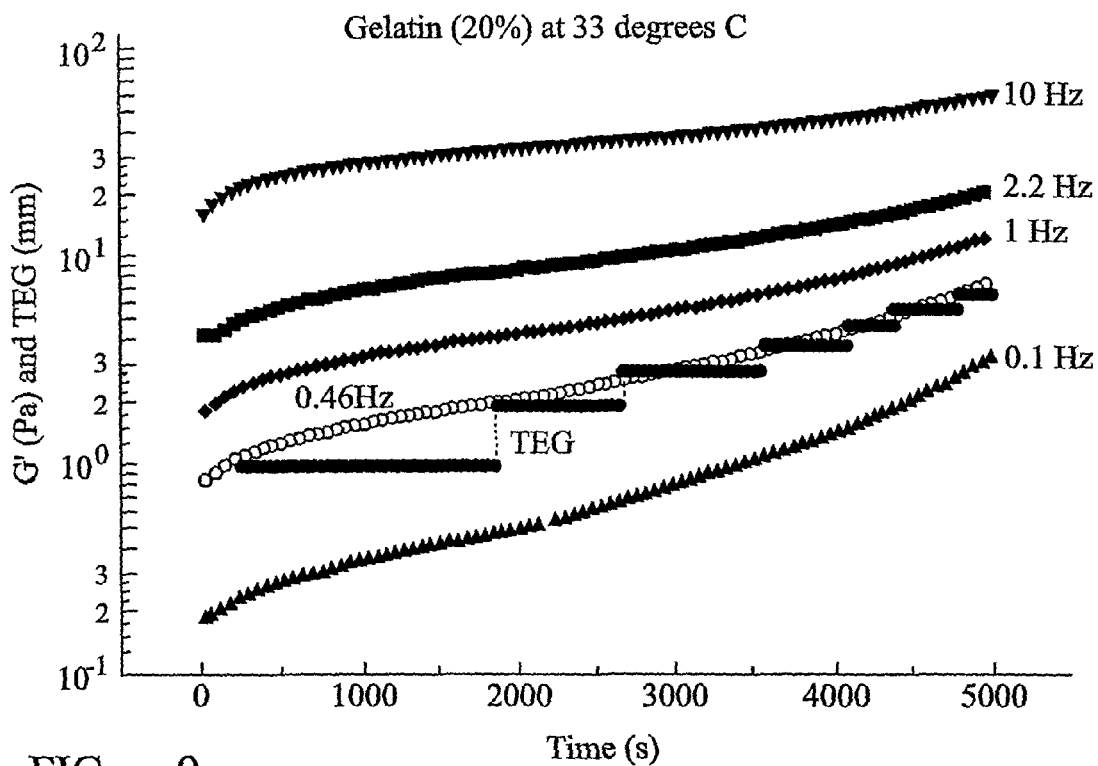
Figure 10:
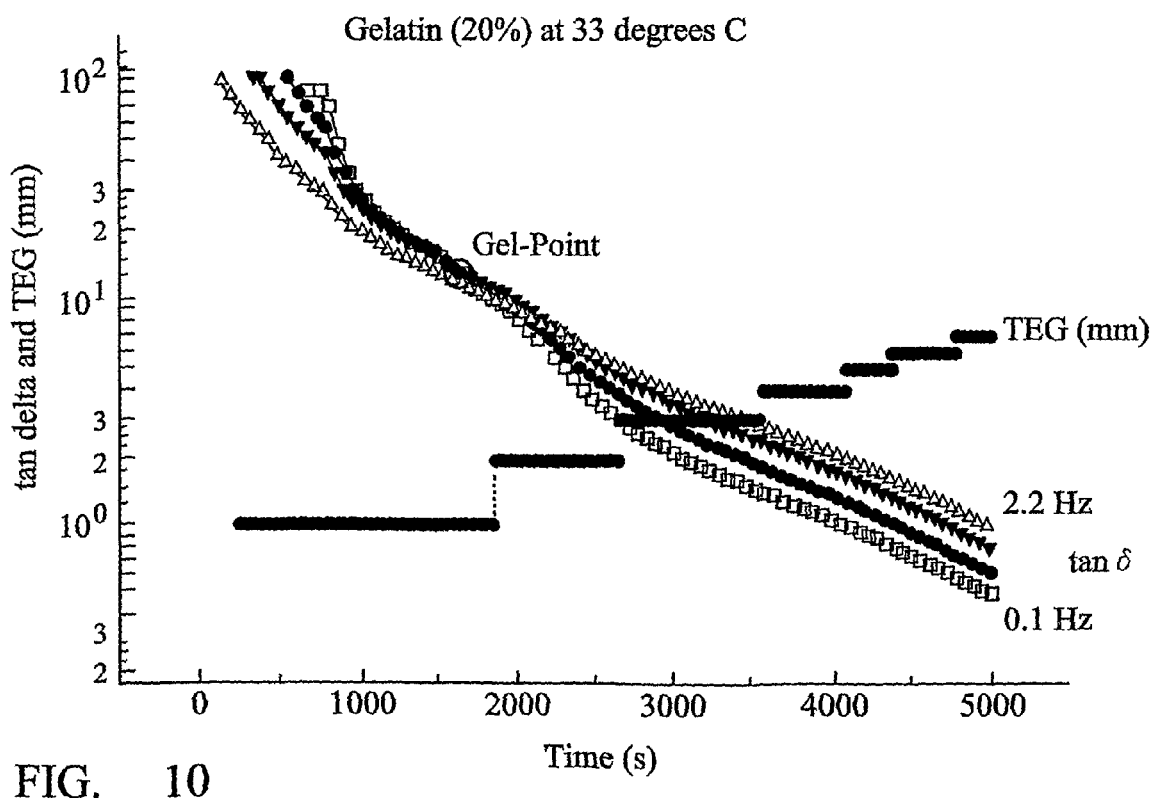
Figure 11:
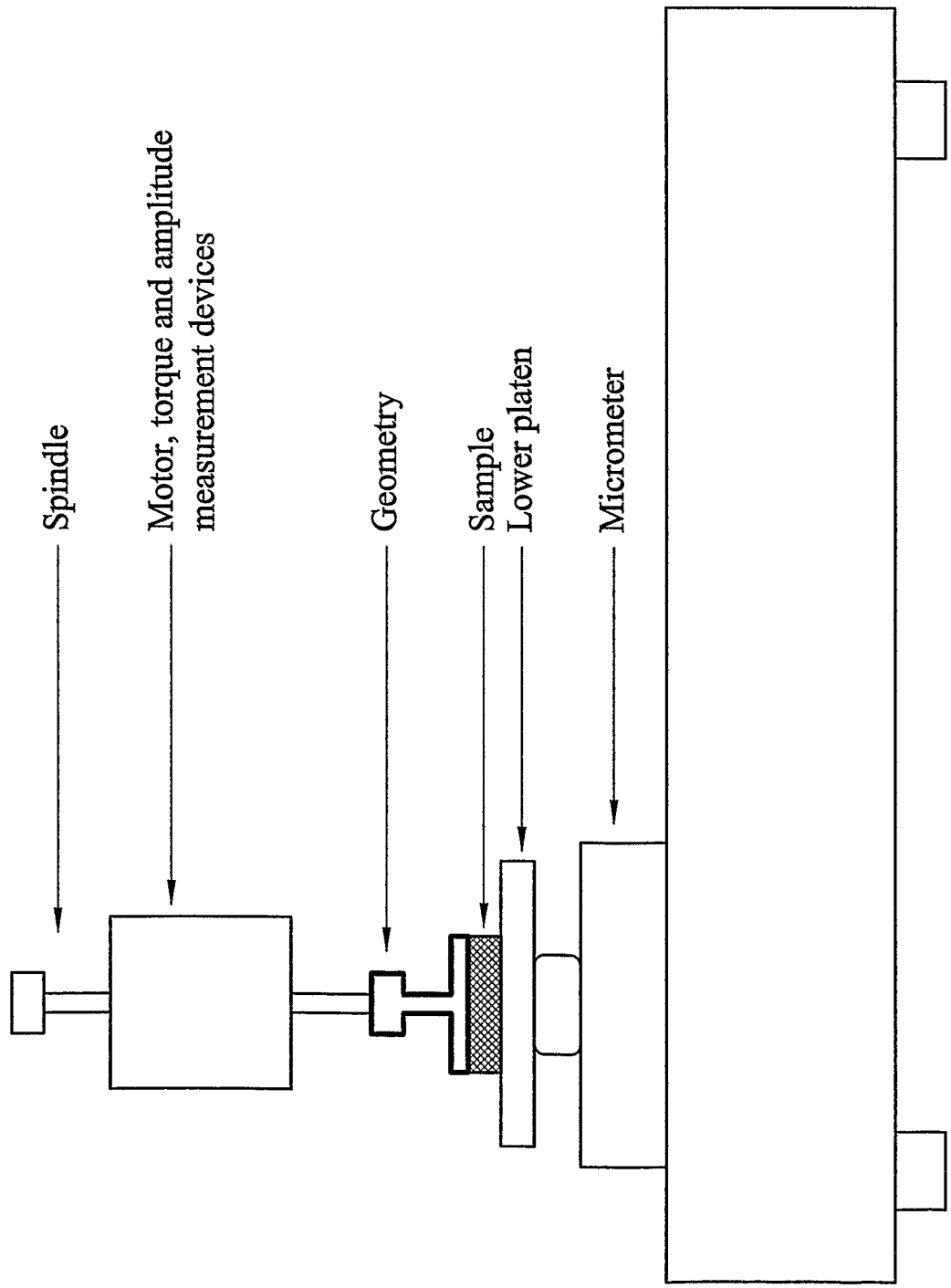

Secondly, the high value of δ at the GP is indicative of a system whose complex shear modulus is dominated by its viscous component, the loss modulus G". It follows that a GP criterion based on measurements of dynamic rigidity (i.e. the shear elastic modulus) are likely to result in considerable overestimates of gelation time, due to the fact that G' must reach some (arbitrary) value. That value varies considerably (as does the oscillation frequency of measurement), and its choice is influenced by the sensitivity and rheometer employed. An example which serves to illustrate the point under discussion may be found in recent studies of fibrin-thrombin gels in which the formation of a clot was associated with the time at which G' attained a value of 0.73 Pa, at a frequency of 0.1 Hz. Clearly, from the present work, such a definition would result in a considerable overestimate of the clotting time for the results shown in FIG. 7 in which G' (measured at 2 Hz) remains at very low levels (<0.1 Pa) for several minutes after the GP. This point has wider significance insofar as measurements of blood clot 'rigidity' are the basis of clotting time assessments in thromboelastography.

In another aspect of the invention called a high frequency rheometer (HFR) the surfaces of the measuring geometry may consist of two or three plane parallel blade-like surfaces A, B, and C immersed in a sample of blood. Surface A undergoes harmonic displacement by electrostrictive actuation, thereby generating high audio frequency transverse shear waves which are reflected at B and C, the latter situated at distances $x_1$ and $x_2$ respectively from A, such that $Dx=x_1-x_2$. Surfaces B and C are connected to transducers such as piezo-crystals which produce voltages in response to the motion of A, which are used to record wave propagation in the sample as it undergoes coagulation. Analysis of measurements rely upon the rapid sampling (1 MHz) of the waveforms at two, spatially separated surfaces. Absolute values of stress and strain are not required, only their relative phases. The Fourier Transform is used to analyse this phase information in the frequency domain, thereby implementing Fourier Transform Mechnical Spectroscopy (FTMS).

Samples undergoing coagulation are subjected to a a composite strain, g, of the following form:

$$\gamma = \sum_{i=1}^{m} \gamma(\omega_i) = \sum_{i=1}^{m} \gamma_i \sin \omega_i t$$

where m is the number of frequency components, $\gamma_i$ is the amplitude of the $i^{th}$ shear strain component and $w_i$ is the $i^{th}$ angular frequency component. Test waveforms are formed by concatenation of two, separate multiplexed waveforms, each having identical frequency components but different amplitudes, resulting in a multiple frequency test waveform with two regions of different maximum amplitude. This ensures that the linearity of the system's response to shear wave propagation can be determined in a single measurement by inspecting each region for amplitude independence of v and δ at each test frequency individually. The strain amplitudes for each frequency component are chosen so that linearity was not exceeded.

When implemented on conventional rheometers incorporating displacement and torque measuring systems, FTMS involves individual frequency components which are integer multiples of a fundamental frequency (Scanlan and Winter, 1991). However, the HFR does not rely on the absolute determination of stresses and strains, and thus there is no requirement to use harmonically related frequencies: rather, anharmonically related frequencies may be employed to mitigate against constructive interference effects, a procedure which serves to moderate the resulting total strain amplitude.

The shear wave signals are subjected to FFT cross-correlation which allows the phase velocity $v_i$ of each frequency component to be determined, thereby yielding $G'(\omega_i)$ and $G''(\omega_i)$ for the frequencies $\omega_i$. The (relatively) high frequencies employed in the HFR allow the rapid sequential measurements (1 sec) essential if each is to be considered as being made upon a time invariant system, and a prerequisite for obtaining accurate phase information.

In order to monitor the entire gelation process in a single experiment, the gaps $x_1$ and $x_2$ may be maintained at pre-set values or adjusted during the course of measurement. Typically the HFR is linked to a data acquisition system fitted with three, 1 MHz analogue-to-digital converters (ADC's), each with 8-Megasample memory and a 5 MHz digital-to-analogue convertor (DAC) with 200 volt output. FFT analysis is carried out on a microcomputer.

The invention claimed is:
1. A method of determining the clotting or gelling characteristics of coagulating blood, the method comprising:
   a) providing a sample of whole blood;
   b) carrying out the following steps using a rheometer:
      i) applying a harmonically time-varying stress, of controlled amplitude and frequency, to the blood at a predetermined first frequency and measuring the corresponding phase and amplitude of the resulting first strain output;
      ii) applying a harmonically time-varying stress, of controlled amplitude and frequency, to the blood at a predetermined second frequency and measuring the corresponding phase and amplitude of the resulting second strain output; and simultaneously
      iii) applying a harmonically time-varying strain, of controlled amplitude and frequency, to the blood at a predetermined first frequency and measuring the corresponding phase and amplitude of the resulting first stress output; or
      iv) applying a harmonically time-varying strain, of controlled amplitude and frequency, to the blood at a predetermined second frequency and measuring the corresponding phase and amplitude of the resulting second stress output;
   c) utilizing a relationship between dynamic rigidity G', loss modulus G", viscoelastic stress relaxation exponent α and angular frequency $\overline{\omega}$;
   d) monitoring a change in G"/G' with time to establish the time at which the blood first gels or clots wherein each frequency of the harmonically time-varying stress or harmonically time-varying strain that is applied to the blood is measured consecutively and each frequency is composed of more than one harmonic frequency formed by concatenation of two separate multiplexed waveforms each having identical frequency components but different amplitude so that dynamic properties of the blood is measured over time as the blood gels or clots.

2. The method as claimed in claim 1, wherein the relationship between dynamic rigidity G', loss modulus G", viscoelastic stress relaxation exponent α, and angular frequency $\overline{\omega}$ comprises the small amplitude oscillatory shear approximation to the Chambon-Winter Gel Equation:

$G'(\overline{\omega})=G''(\overline{\omega}) / (\tan \alpha\pi/2)$; or wherein the relationship $\tan \delta=G''/G'$ is monitored with time to establish the time at which $\tan \delta=G''/G'$ is the same irrespective of the frequency applied in steps b) and c) so as to establish the time when the blood first forms a clot.

3. The method as claimed in claim 2, wherein the results for the clots formed utilizing said method utilize values of $\alpha$ in the range of $0<\alpha<1$; and/or wherein the method determines the instant at which a sample of coagulating blood undergoing gelation from one in which only short range connectivity is present to one in which a 3- dimensional structure is sample-spanning, and represents the gel point, which precedes the clotting time indicated by a thromboelastograph; and/or wherein the method provides a framework for the quantification of structural complexity in clots formed under a range of biophysical and biochemical conditions; and/or wherein the method uses the rheometer of the controlled, forced non-resonant oscillatory displacement type or the oscillatory torque type; and optionally wherein said rheometer has "strain-in" and "torque-out" electrical signal sockets.

4. The method as claimed in claim 3, wherein said rheometer is designed to perform both steady and dynamic measurements.

5. The method as claimed in claim 3, wherein the rheometer processes data using analysis software; and/or wherein the rheometer allows the user to perform their own calculations upon unprocessed data; and/or wherein said rheometer includes one or more of the following: a low shear actuator, a force re-balance transducer and an environmental system.

6. The method as claimed in claim 3, wherein the rheometer comprises one or more of the following:
 i. an air bearing;
 ii. a hollow spindle incorporating a threaded draw rod, onto which measuring geometry is secured;
 iii. a digital encoder for sensing angular displacement;
 iv. a non-rotating platen of the measuring geometry; and
 v. a temperature control unit.

* * * * *